United States Patent [19]

Lindmayer et al.

[11] Patent Number: 4,623,332
[45] Date of Patent: Nov. 18, 1986

[54] NEEDLELESS JET INJECTOR

[75] Inventors: Istvan Lindmayer, Pierrefonds; Karim Menassa, St. Laurent, both of Canada

[73] Assignee: Patents Unlimited Ltd., Hamilton, Bermuda

[21] Appl. No.: 485,046

[22] Filed: Apr. 14, 1983

[51] Int. Cl.⁴ ........................................... A61M 11/00
[52] U.S. Cl. ..................................... 604/68; 604/135
[58] Field of Search ............. 604/48, 68, 72, 131–136, 604/143

[56] References Cited

U.S. PATENT DOCUMENTS

| | | | |
|---|---|---|---|
| 63,339 | 10/1882 | Dettbarn | 604/68 |
| 843,520 | 8/1960 | Wise | 604/68 |
| 1,205,551 | 9/1970 | Sinclair | 604/135 |
| 1,333,215 | 10/1973 | Bissell | 604/68 |
| 2,704,543 | 3/1955 | Scherer | 604/68 |
| 3,490,451 | 1/1970 | Yahner | 604/68 |
| 3,507,276 | 4/1970 | Burgess | 604/135 |
| 3,908,651 | 9/1975 | Fudge | |
| 4,165,800 | 8/1979 | Doherty | 604/68 |
| 4,447,225 | 5/1984 | Taff et al. | |
| 4,518,385 | 5/1985 | Lindmayer et al. | 604/68 |

Primary Examiner—Stephen C. Pellegrino
Assistant Examiner—Mark Rooney
Attorney, Agent, or Firm—Wegner & Bretschneider

[57] ABSTRACT

A needleless hypodermic injector includes an elongated cylindrical casing defined by front and rear telescoping sections, with an injection orifice at the closed front end of the front section and a push button trigger at the rear end of the rear section. A piston slidably mounted in a cylinder in the front section of the casing moves rearwardly to define a medicine chamber for receiving medicine from a bottle directly or through a valve incorporated in the front end of the front casing section. The piston is moved rearwardly by an internally threaded collar on the externally threaded cylinder, the collar pressing against a bushing, which presses against disc springs in the rear section of the casing. A latch mechanism retains the bushing against the springs until the trigger is pressed, at which time the springs drive the piston forward to discharge the medicine from the chamber through the injection orifice.

2 Claims, 12 Drawing Figures

NEEDLELESS JET INJECTOR

BACKGROUND OF THE INVENTION

1. Field of the Invention

This invention relates to a hypodermic injector, and in particular to a compact, needleless hypodermic injector.

The needleless injection of medicines into the body is decidedly preferable to the old fashioned needle and syringe. A needleless jet injector makes a substantially smaller hole than a needle, and consequently needleless injection is less painful than injection with a needle. Moreover, for people requiring frequent injections, e.g. diabetics, needleless injection, which results in less damage to the skin and tissue, is definitely preferable. This is an important consideration, since the areas on the body which can be used for injection are limited. However, needleless jet injectors have met with somewhat limited success.

2. Discussion of the Prior Art

Needleless jet injectors of generally the same type disclosed and claimed herein are the subject of many patents, including, for example Canadian Pat. No. 569,887, issued to R. P. Scherer on Feb. 3, 1959, and U.S. Pat. Nos. 2,928,390 issued to A. Venditty et al on Mar. 15, 1960; 3,202,151, issued to A. W. Kath on Aug. 24, 1965; 3,292,621, issued to O. H. Banker on Dec. 20, 1966; 3,292,622, issued to O. H. Banker on Dec. 20, 1966; 3,518,990, issued to O. H. Banker on July 7, 1970; 3,561,443, issued to O. H. Banker of Feb. 9, 1971; 3,688,765, issued to J. S. Gasaway on Sept. 5, 1972; 3,815,594, issued to N. R. Doherty on June 11, 1974 and 4,059,107, issued to N. Iriguchi et al on Nov. 22, 1977. Few of the devices disclosed by these patents are available in the marketplace. Many of the devices lack simplicity, i.e. are expensive to produce or use. The gas cylinders used in some of the injectors are expensive and difficult to find, and without such cylinders the devices are useless. Moreover, the pressure in such cylinders may vary. Of even greater importance is the failure of such injection devices to achieve the pressures required for proper injection. In order to effect a needleless injection properly, a high initial pressure is required to pierce the skin. Once the skin has been pierced, the pressure should drop substantailly to an injection pressure. The injection pressure should be such that all of the medicine is injected to a predetermined depth in the tissue, i.e. into the fat beneath the skin and not into the muscle. The injection pressure is determined by the back pressure in the tissue. As the medicine is injected, the back pressure in the tissue builds up to a maximum, which is substantially less than the pressure required to pierce the skin. The injection pressure should either rise with such back pressure or be maintained at a constant level at least equal to the maximum back pressure. Otherwise, there is a very real danger that the medicine being injected will be forced out of the tissue at the end of the injection step. If the injection pressure is too high, i.e. substantially greater than the maximum back pressure, the danger exists that the medicine will be injected to the incorrect depth such as into the muscle. Injections into the muscle are more painful than subcutaneous injections. With thin people, the distance between the skin and the muscle is small. Moreover, some medicines such as insulin must be injected subcutaneously; otherwise the period of relief provided by the medicine varies. In other words, when using insulin it is obviously important to know how long the effects of injection will last. The absorption time for muscle is much shorter than the absorption time for fat. By injecting subcutaneously, i.e. into the fat, a longer absorption time is obtained. If some of the medicine enters the muscle, there can be a deletereous effect.

It is worthwhile mentioning at this point that one proposal to avoid the use of needles (or for that matter injectors of the type disclosed herein) by diabetics is an insulin pump carried by the diabetic or embedded beneath the skin. While such a proposal may have its merits, for a variety of reasons including vanity, people are often loath to carry either externally or internally any contrivance which labels them as having a disease or illness of any type.

There still exists a need for a simple, yet effective needleless jet injector. The object of the present invention is to meet such need by providing a relatively simple needleless jet injector, which is capable of producing the pressure required for proper administration of a medicine. By proper administration is meant injection of the entire dose to the desired depth, i.e. subcutaneously.

GENERAL DESCRIPTION OF THE INVENTION

Accordingly, the present invention relates to a needleless hypodermic injector comprising a casing defining a medicine chamber and a pressure chamber; means for introducing medicine into said medicine chamber; an injection orifice for discharging medicine from said medicine chamber; piston means slidably mounted in said medicine chamber for movement between a retracted position in which said medicine chamber contains medicine, and an extended position in which the medicine is completely discharged from said medicine chamber; and drive means for driving said piston means from the retracted position to the extended position at discharge pressures such that the skin is initially pierced and thereafter the discharge pressure is slightly greater than the back pressure of the fluids in the tissue throughout the remainder of the injection.

It will be appreciated that the ideal discharge pressure is that pressure sufficient to maintain injection without injecting into the muscle.

BRIEF DESCRIPTION OF DRAWINGS

The invention will now be described in greater detail with reference to the accompanying drawings, which illustrate preferred embodiments of the invention, and wherein.

DESCRIPTION OF PREFERRED EMBODIMENTS

Figure 3:
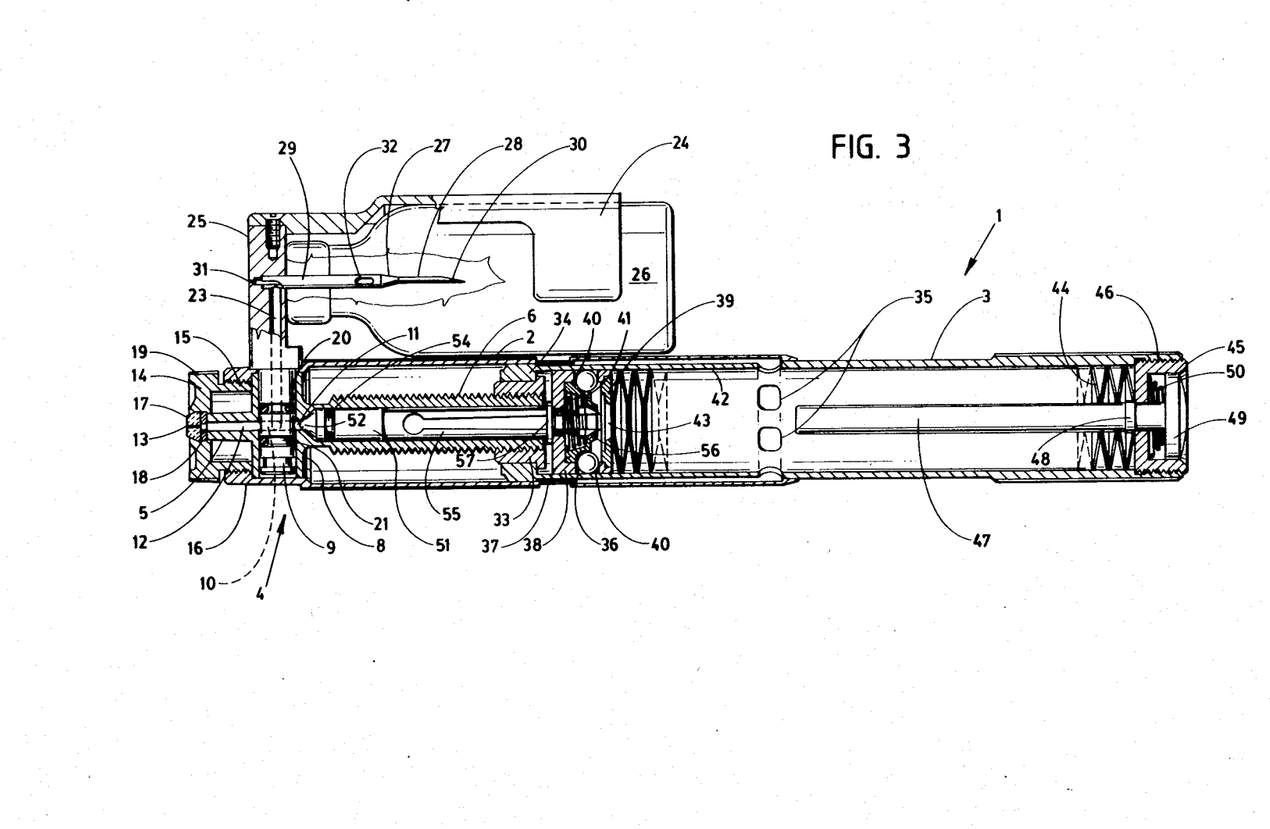
FIGS. 3 and 4 are longitudinal sectional views of the device of FIGS. 1 and 2 in the rest or extended position and the retracted position, respectively.
Figure 4:
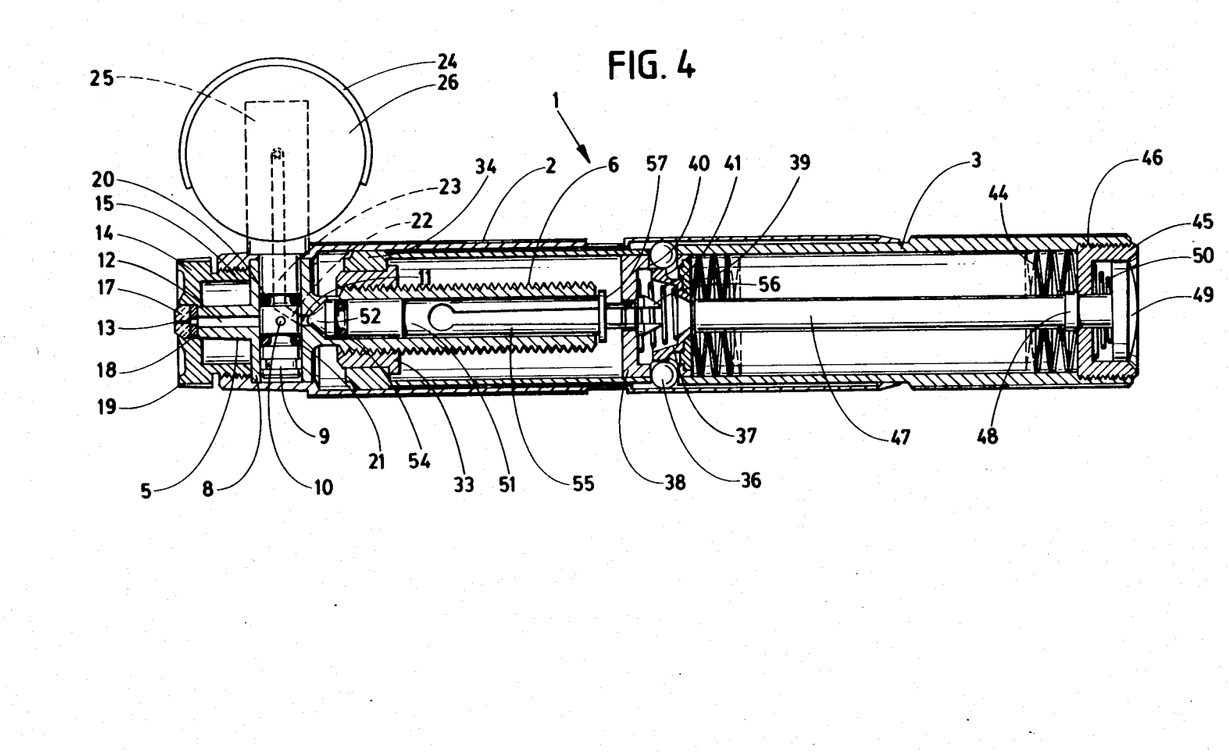

With reference to FIGS. 1 to 4, one embodiment of the present invention includes a casing generally indicated at 1. The casing 1 is defined by cylindrical, telescoping sections 2 and 3, hereinafter referred to as the front and rear sections, respectively. In this case, front refers to the discharge end, and rear refers to the handle end of the casing 1. The rear section 3 of the casing 1 is mounted in the front section for movement between the extended or rest position (FIG. 3) and the retracted position (FIG. 4).

The front section 2 of the casing 1 contains a valve generally indicated at 4 through which medicine is introduced into and discharged from the casing 1. A forwardly extending discharge tube 5 and a rearwardly extending cylinder 6 are integral with the valve 4. The valve 4 includes a transversely extending tube 8 for receiving a valve stem 9. A straight passage 10 in the valve stem 9 allows for fluid communication between a discharge opening 11 in the otherwise closed front end of the cylinder 6 and a discharge passage 12 in the tube 5. Medicine passing through the passage 12 is discharged from the device via a discharge orifice 13 in an injection head 14, which is removably mounted on the front end of the casing 1.

The injection head 14 includes an externally threaded cylindrical body 15 for threadedly engaging the internally threaded front end 16 of the casing 1. An insert 17 containing the discharge orifice 13 is mounted in the head 14, with an annular gasket 18 providing a seal between the discharge tube 5 and the head 14. The outer periphery 19 of the head 14 is knurled to facilitate manual removal or insertion thereof.

The valve stem 9 is rotatably mounted in the sleeve 8. The stem 9 is sealed in the sleeve 8 by O-rings 20 and 21 on either side of the passage 10. A second, inclined passage 22 is provided in the valve stem 9 at 90° to the passage 10. The passage 22 communicates with a passage 23 extending longitudinally of the stem 9. The valve stem 9 extends upwardly out of the casing 1. A bracket 24 connected to the outer end 25 of the valve stem 9 releasably holds a medicine container 26. The container 26 is a standard medicine bottle with a rubber cap, containing a quantity of medicine sufficient for multiple injections. When the container 26 is empty, a new container is mounted in the bracket 24.

A needle 27 mounted in the outer end 25 of the valve stem 9 introduces medicine from the container 26 into the passage 23. The needle 27 is defined by coaxial tubes 28 and 29. The inner tube 28 is a straight needle with a pointed inner end 30. An orifice 31 in the stem 9 introduces air into the tube 28. The outer tube 29 contains a pair (one shown) of opposed inlet openings 32 through which medicine enters the needle 27 and consequently the passage 23.

The cylinder 6 is externally threaded for receiving an internally threaded ring 33 (FIGS. 3 and 4), which is press fitted to an annular, inwardly extending flange 34 on the front end of the casing section 3. Thus, rotation of the rear casing section 3 with respect to the section 2 causes movement of the section 3 into the front section 2. Movement of the rear section 3 into the front section 2 of the casing 1 is limited by a latch mechanism.

The latch mechanism includes a plurality (in this case six) of apertures 35 arranged in a circle in the rear casing section 3, and an equal number of balls 36 also located in such rear section 3. When the balls 36 and holes 35 are aligned, the balls are forced into the holes 35 by a stepped collar 37. The collar 37 and balls 36 are mounted in a chamber defined by a cup-shaped bushing 38, which is slidable in the rear casing section 2, and a cap 39 on the bushing 38. The bushing 38 contains holes 40 longitudinally aligned with the holes 35, so that when the casing sections 2 and 3 are moved together sufficiently, the balls enter the holes to lock the casings together in the retracted position (FIG. 4). A tapered helical spring 41 in the collar 37 biases the collar and the balls 36 towards the cap 39. In the extended position of the casing 1 (FIG. 3), the balls bear against the interior surface 42 of the casing section 3. When the holes 35 and 40 become aligned, the balls 36 are pushed into the holes 40 by the spring 41 and the collar 37. Rearward movement of the collar 37 is limited by the cap 39, which has a tapered aperture 43 for receiving the tapered rear end of the collar 37.

When the casing sections 2 and 3 move together a stack or row of disc springs 44 is compressed between the cap 39 and an end cap 45 on the casing section 3. The end cap 45 is generally cup-shaped and externally threaded for mounting in the internally threaded end 46 of the casing section 3. Thus, the cap 45 can be removed for decreasing or increasing the number of disc springs 44. A rod 47 extends through the cap 45 into the aligned apertures in the springs 44 in the rear casing section 3. An annular shoulder 48 on the rod 47 retains the rod in the cap 45. A push button 49 is provided on the outer end of the rod for sliding movement in the cap 45. The button 49 is biased outwardly by a tapered helical spring 50, so that the rod 47 is normally in the rearmost or outermost position.

A piston 51 is slidably mounted in the cylinder 6 in the front casing section 2. The piston 51 includes a tapered front end 52 for mating with a correspondingly tapered front end of the chamber 53 (FIGS. 5 to 8) in the cylinder 6 surrounding the discharging opening 11. The tapered front end 52 of the piston 51 and corresponding tapered front end of the chamber 53 ensure that the maximum quantity of liquid is discharged from the chamber 53 when the piston 51 moves forwardly. The piston 51 is sealed in the chamber 53 by an O-ring 54. The rear end 55 of the piston 51 is bifurcated, the arms thereof extending rearwardly into the chamber containing the balls 36, collar 37 and spring 41. When the piston 51 moves forwardly, rearwardly tapering heads 56 on the rear ends of the arms of the piston 51 engage the bushing 38 to move the entire rear casing section 3 and its contents forwardly into the front casing section 2. A washer 57 on the rear end 55 of the piston 51 moves the bushing 38 and cap 39 rearwardly when the casing sections 2 and 3 are moved together. The outer surfaces of the front end of the front casing section 2 and the rear end of the rear casing section 3 are knurled at 58 and 59 to facilitate manual operation of the injector. An indicator window 60 (FIGS. 1 and 5) is provided in one side of the front casing section 2 for indicating dosages as described hereinafter in greater detail. The numbers indicating the dosages are provided on the outer surface of the rear casing section 3 in the front casing section 2. The numbers are arranged in a helical path on the rear casing section 3, so that as the section 3 moves rearwardly consecutive numbers appear in the window 60.

Figures 1, 2, 5:
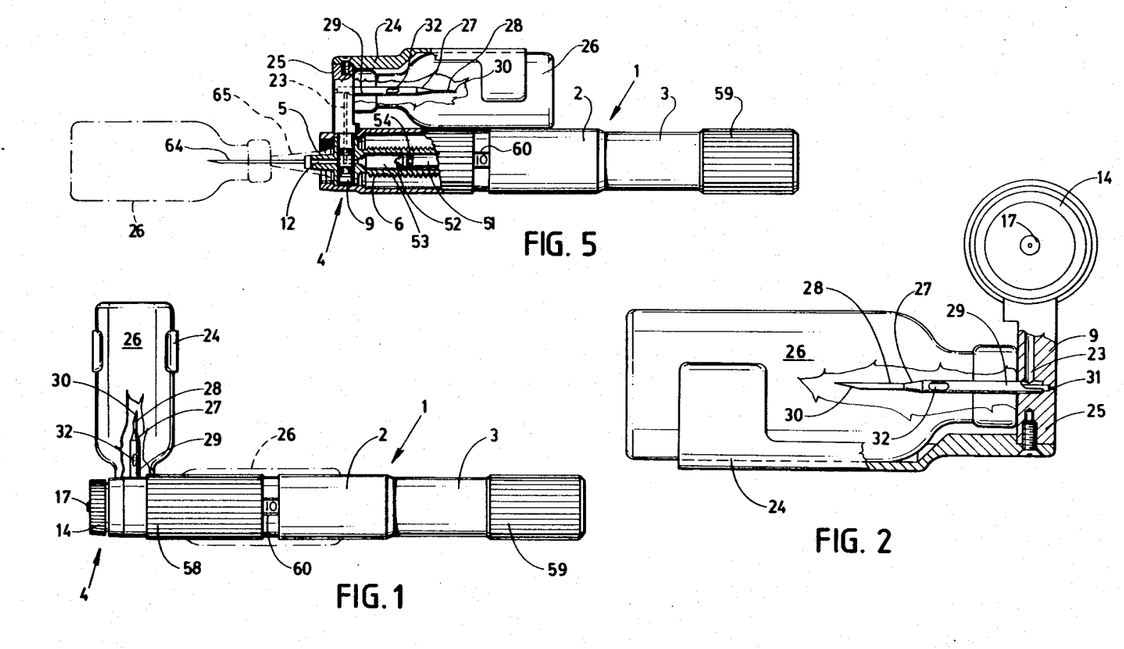
FIG. 1 is an elevation view of one embodiment of needleless jet injector in accordance with the present invention.
FIG. 2 is a partly sectioned front end view of the device of FIG. 1.
FIG. 5, which appears on the first sheet of drawings, is a partly sectioned elevation view of the device of FIGS. 1 to 4 during filling with a medicine.

A second embodiment of the invention will now be described with reference to FIGS. 6 and 7, in which wherever possible the same reference numerals have been used to identify the same elements as in FIGS. 1 and 2.

Figure 6:
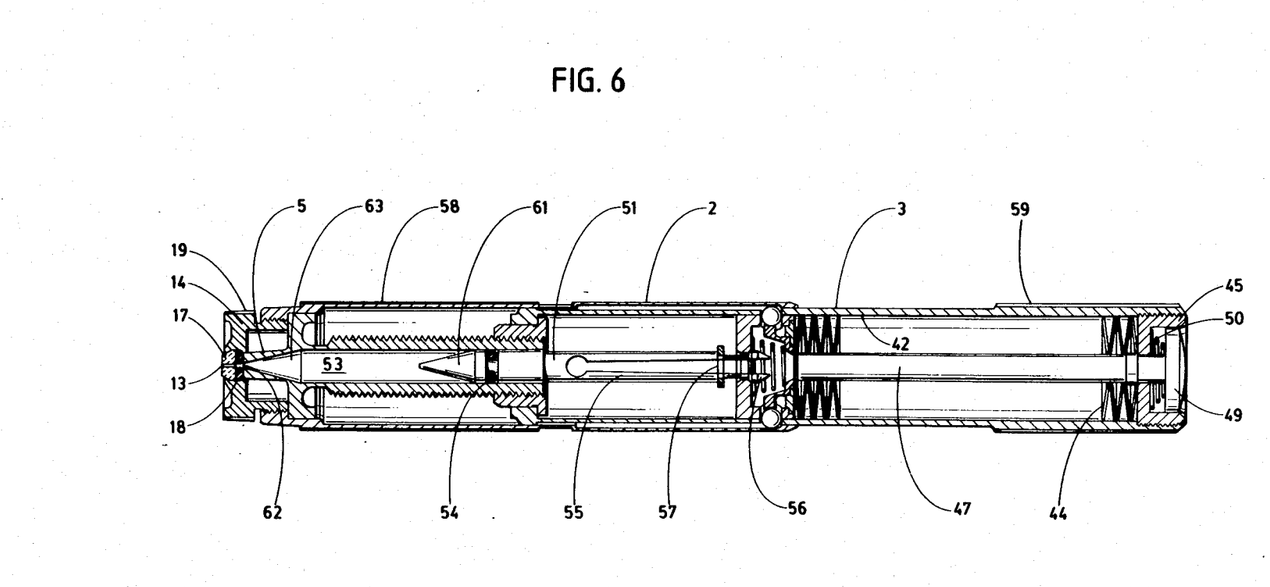
FIG. 6 is a longitudinal sectional view of a second embodiment of injector in accordance with the present invention in the retracted position.
Figure 7:
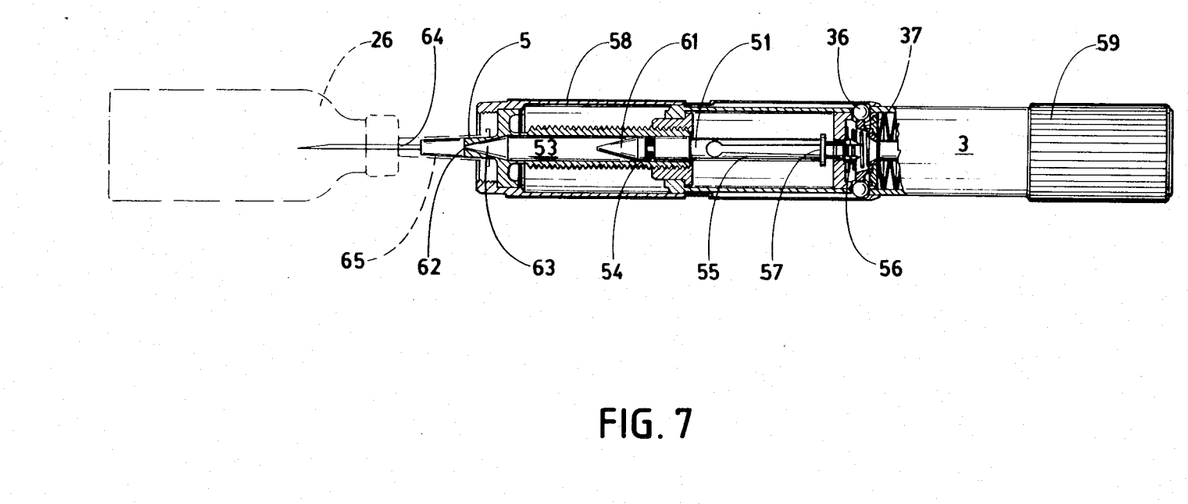
FIG. 7 is a partly sectioned elevation view similar to FIG. 6 illustrating the filling of the injector of FIG. 6.

In the device shown in FIGS. 6 and 7, the valve and container bracket are omitted from the front end of the front casing section 2, and the piston 51 is provided with a conical front end 61 for sealing an orifice 62 at the front end of a forwardly tapering discharge passage 63 in the discharge tube 5. The chamber 53 in the cylinder 6 created by rearward movement of the piston 51 is filled with medicine by removing the injection head 14 and substituting a needle 64. For such purpose, the tube 5 has the same taper as the funnel 65 on a standard disposable needle 64. The needle 64 is inserted into the bottle 26 and, as the piston 51 is retracted, the chamber 53 is filled with medicine.

Figure 8:
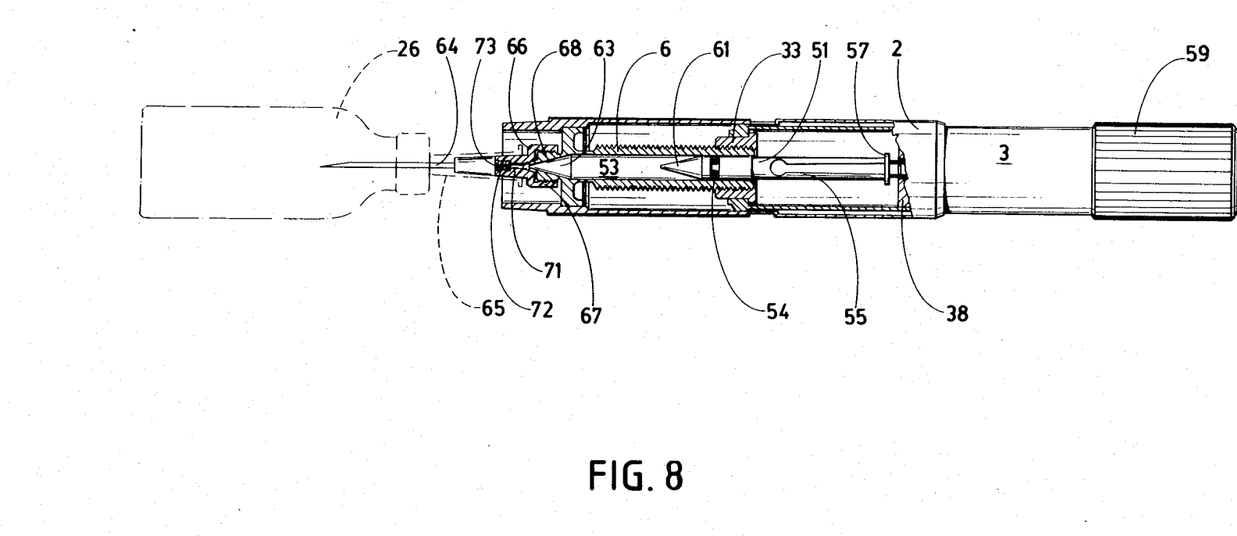
FIG. 8 is a partly sectioned elevation view of a slightly modified version of the device of FIGS. 6 and 7.
Figure 9:
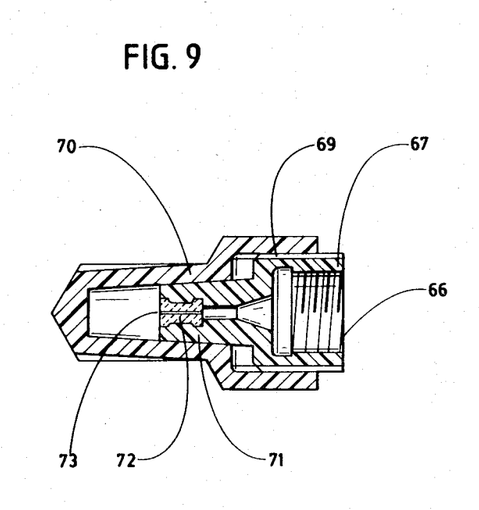
FIG. 9 is a longitudinal sectional view of an injection head and cover used in the device of FIG. 8.

FIGS. 8 and 9 of the drawings, illustrate disposable injection heads 66, each of which includes an internally threaded tube 67 for mounting on an externally threaded discharge tube 68. The tube 67 of the head 66 of FIG. 9 includes longitudinally extending ribs 69 for engaging similar ribs in a cover 70. Each of the heads 66 includes a discharge tube 71 containing an insert 72, with an injection orifice 73 therein.

Figure 10:
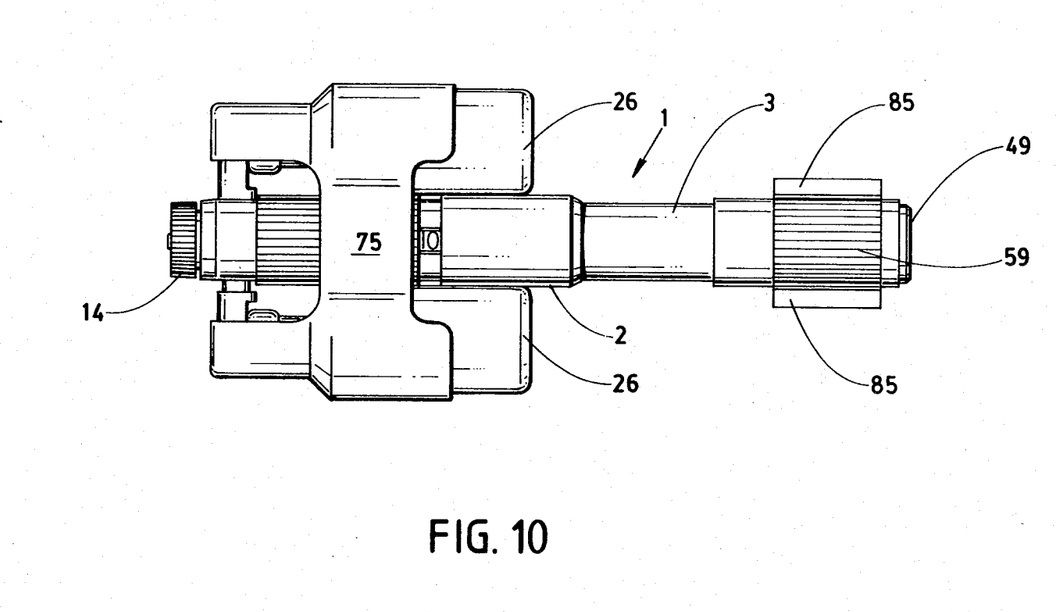
FIG. 10 is an elevation view of another embodiment of the injector of the present invention.
Figure 11:
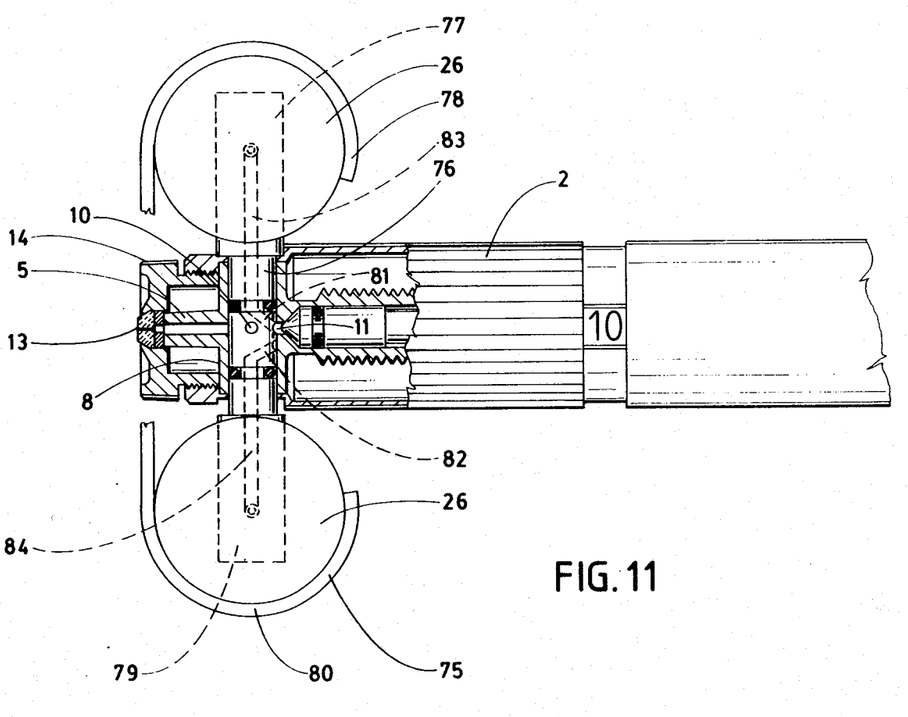
FIG. 11 is a partly sectioned elevation view of the injector of FIG. 10 showing filling of the injector.

Referring now to FIGS. 10 and 11, there is shown an embodiment of the invention similar to that of FIGS. 1 to 5, except that the single bracket 24 is replaced by a bracket 75 for carrying a pair of medicine containers 26. A valve stem 76 carrying the bracket 75 extends radially outwardly from opposed sides of the front casing section 2, one end 77 connected to one sleeve 78 for carrying a medicine bottle 26 and the other end 79 connected to another sleeve 80 for carrying a second medicine bottle 26. The stem 76 is rotatable and slidable in the sleeve 8. A pair of inclined passages 81 and 82 are provided in the stem 76 communicating with passages 83 and 84 extending longitudinally of the stem 76 for connecting the discharge opening 11 to one or the other of the bottles 26.

Another minor modification included in the device of FIGS. 10 and 11 is the provision of a pair of opposed rectangular wings or arms 85 on the knurled rear end of the casing section 3 for facilitating manual operation of the device. The push button 49 also extends a greater distance out of the casing 1 than in the other embodiments of the invention.

OPERATION

Except for the passages used to load the injectors, each embodiment of the invention operates in essentially the same manner. The rear casing section 3 is rotated relative to the front casing section 2 to cause the ring 33 and consequently the casing section 3 to move forwardly towards the injection or front end of the device. When the section 3 reaches the location in which the balls 36 are aligned with the holes 35, the balls 36 move outwardly, locking the bushing 38 and cap 39 in the extended position (FIG. 4).

With the bushing 38 and piston 51 locked in position, the bottle 26 and the valve stem 9 are rotated so that the passage 22 is aligned with the opening 11 (FIGS. 1 and 3), the funnel end 65 of the needle 64 is placed on the tube 5 or 71 (FIGS. 4 to 8), or the bracket 75 is rotated (out of the plane of the paper) from the position shown in FIG. 10 to align one of the passages 81 and 82 with the opening 11 (FIG. 11). In each case, the rear casing section 3 is rotated in the opposite direction, which causes the front casing section 2 and the cylinder 6 to move away from the rear casing section 3. As the casing sections 2 and 3 start to move apart again, because of the friction of the O-ring 54 in the cylinder 6, the piston 51 initially moves with the cylinder 6 and the casing section 2. The heads 56 on the arms of the piston 51 engage the rear surface of the bushing 38 to prevent further movement of the piston 51 with the cylinder 6, leaving a gap between the front surface of the bushing 38 and the washer 57 (FIGS. 4 and 6 to 8). Continued separation of the casing sections 2 and 3 creates a gap (the chamber 53) between the front end of the piston 51 and the opening 11 or 62. The partial vacuum thus created in the chamber 53 causes medicine to be sucked into the chamber.

It is readily apparent that all embodiments of the invention can be used to administer a mixture of medicines, e.g. slow and fast acting insulins. With the first embodiment of the invention, the injection head 14 is removed. Some medicine is drawn into the chamber 53 from the bottle 26 attached to the casing 1 by the bracket 24 (FIG. 1). Then, by placing a second bottle 26 and needle 64 on the tube 5 and rotating the valve stem 9 to align the opening 11 and passages 10 and 12, medicine can be drawn into the chamber 53 from the second bottle 26 (FIG. 5).

The devices shown in FIGS. 6 to 8 are filled with separate medicines merely by changing bottles 26 during a filling operation. With the injector of FIGS. 10 and 11, the bracket 75 and the bottles 26 are rotated from the closed position (FIG. 10) in which the bottles are aligned with the casing 1 to the filling position (FIG. 11) in which the bottles 26 are at right angles to the casing 1. In the filling position one inclined passage 81 is in fluid communication with the opening 11. After the desired amount of the medicine has been withdrawn from the first bottle 26, the bracket 75 is pushed so that the valve stem 76 slides in the sleeve 8 to place the second inclined passage 82 in fluid communication with the opening 11, and filling of the chamber 53 is completed.

Figure 12:
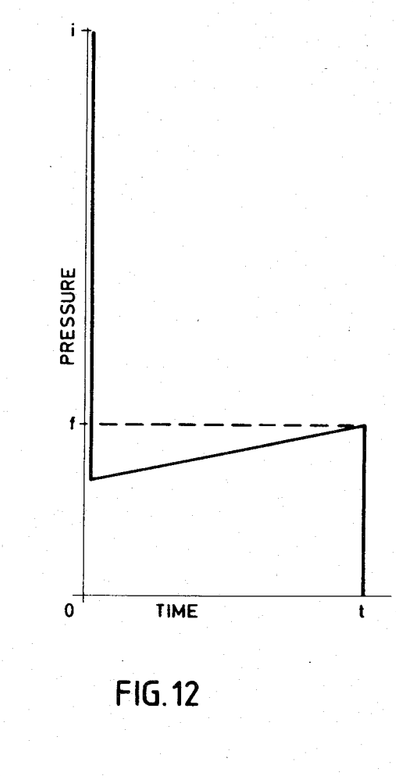
FIG. 12, which appears on the seventh sheet of drawings, is a schematic graph illustrating the changes in injection pressure for the injector of the present invention.

With the chamber 53 full the bracket 24 or 75 is rotated or the needle 27 or 64 is removed and the injection head 14 or 66 is replaced on the front end of the casing 1. The injection insert 17 or 72 is placed against the skin, and the button 49 is pushed. The rod 47 moves forwardly against the rear end of the collar 37, pushing the collar forward which permits the balls 36 to escape from the holes 35. The bushing 38 moves rapidly forward against the washer 57 to provide the pressure required to pierce the skin. The gap between the washer 57 and the bushing 38 in the loaded condition of the injector causes the bushing 38 to hit the washer 57 with sufficient force to cause piercing of the skin by the jet of medicine. Thus, the initial pressure i (FIG. 12) of the jet is quite high. The pressure drops rapidly to below the final pressure f, which equals the final back pressure in the tissue. As the injection progresses, the jet pressure rises to pressure f at the time t which represents the end of the injection at which time the piston has returned to the front of the cylinder 6 (FIG. 3).

It has been found that for proper injection, the injector must provide a high energy jet to pierce the skin. Once the skin has been pierced, the energy can be substantially reduced, but must not decrease below a certain level, namely the level of the final back pressure. The skin is pierced by a very small quantity of medicine in a relative short period of time (approximately 1/100 of a second). The remainder of the medicine is injected at the lower constant or increasing pressure.

The present inventors have determined that the desired pressure characteristics are obtained by the use of disc springs. During extension, such springs can keep the pressure constant or increase the pressure (see Almen, I. O. and Laszlo, A. "The UniformSection Disc Spring" Trans. ASME 58 (1936) pages 305 to 314). By "constant" in this case is meant substantially constant, i.e. varying within a small range. According to this reference and experiments by the inventors, under certain conditions when the height (h) of the disc spring divided by the thickness (t) of the material (h/t) equals $\sqrt{2}$, the pressure on the section of deflection is constant. When h/t is higher than $\sqrt{2}$, e.g. 1.5 to 1.8, the pressure increases during extension. By providing proper disc springs in series, the desired pressure and pressure curve can be achieved. The pressure of a set of disc springs in the casing can readily be changed by doubling one or more of the disc springs. The spring arrangement can be used in manual, foot, pneumatic or electrically operated devices, i.e. devices which are moved manually, by foot, pneumatically or electrically from the extended to the retracted position. With a helical spring, the pressure invariably decreases as the spring extends.

We claim:

1. A needleless hypodermic injector, comprising:
   a first substantially cylindrical section and a second substantially cylindrical section movably mounted in a first end of the first section;
   wherein the first section comprises a hollow cylinder defining a chamber for a substance to be administered, the chamber having therein an orifice at a second end of the first section, and a piston slidably mounted in the hollow cylinder; and
   the second section comprises spring means in the form of a plurality of disc springs for driving the piston in the first section from a retracted position in which the hollow cylinder contains the substance to be administered to an extended position in which the substance is substantially completely discharged through the orifice from the chamber; a bushing slidably mounted between the piston and the spring means and engaging the piston as it travels from the retracted position to the extended position; and latch means for locking the bushing and thereby the spring means in the retracted position;
   a washer means on said piston spaced from the bushing toward the orifice when the bushing is locked in the retracted position by the latch means;
   whereby, when the latch means is released from the bushing, the spring means drives the bushing against the washer means, driving the piston toward the orifice in the hollow cylinder to provide a skin piercing pressure to the substance to be discharged through the orifice and thereafter moves the piston to the extended position.

2. The injector of claim 1, wherein the disc springs are adapted to expand from a compressed state to provide a substantially constant or increasing pressure against the bushing as the bushing moves the piston to the extended position.

* * * * *